(12) United States Patent
Jurado et al.

(10) Patent No.: US 8,211,639 B2
(45) Date of Patent: Jul. 3, 2012

(54) IMAGING GLYPHOSATE IN PLANT TISSUE

(75) Inventors: Luis A. Jurado, St. Louis, MO (US); Maria Cristina Ubach, Chesterfield, MO (US); David Duncan, St. Charles, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 13/255,014

(22) PCT Filed: Mar. 9, 2010

(86) PCT No.: PCT/US2010/026673
§ 371 (c)(1),
(2), (4) Date: Oct. 5, 2011

(87) PCT Pub. No.: WO2010/104861
PCT Pub. Date: Sep. 16, 2010

(65) Prior Publication Data
US 2012/0040339 A1 Feb. 16, 2012

Related U.S. Application Data (60) Provisional application No. 61/158,840, filed on Mar. 10, 2009.

(51) Int. Cl.
*C12Q 1/68* (2006.01)
*A01H 15/00* (2006.01)
(52) U.S. Cl. .......................... 435/6.1; 800/300
(58) Field of Classification Search .......... None
See application file for complete search history.

(56) References Cited

U.S. PATENT DOCUMENTS

| | | | |
|---|---|---|---|
| 5,463,175 A | 10/1995 | Barry et al. | |
| 5,776,760 A | 7/1998 | Barry et al. | |
| 6,746,848 B2 | 6/2004 | Smith | |
| 6,849,430 B2 | 2/2005 | Carson et al. | |
| RE38,825 E | 10/2005 | Barry et al. | |
| 2004/0197793 A1 | 10/2004 | Hassibi et al. | |
| 2004/0197845 A1 | 10/2004 | Hassibi et al. | |
| 2006/0040826 A1 | 2/2006 | Eaton et al. | |

FOREIGN PATENT DOCUMENTS

| | | |
|---|---|---|
| WO | WO 92/00377 | 1/1992 |
| WO | WO 2004/113555 A2 | 12/2004 |
| WO | WO 2010/104861 A1 | 9/2010 |

OTHER PUBLICATIONS

Clegg et al (Development of Enzyme-Linked Immunosorbent Assay for the Detection of Glyphosate (J. Agri. Food Chem. 1999, 47, 5031-5037).*
Shao, Novel cyanobacterial biosensor for detection of herbicides Applied and Environmental Microbiology (2002), 68(10), 5026-5033.*
Ainscow et al., Dynamic imaging of free cytosolic ATP concentration during fuel sensing by rat hypothalamic neurones: evidence for ATP-independent control of ATP-sensitive K+channels, Journal of Physiology, 544.3, pp. 429-445, 2002.
Borisjuk et al., Spatial analysis of plant metabolism: Sucrose imaging within *Vicia faba* cotyledons reveals specific developmental patterns, The Plant Journal, 29(4), pp. 521-530, 2002.
Brecke et al., Effect of Glyphosate on Intact Bean Plants (*Phaseolus vulgaris L.*) and Isolated Cells, Plant Physiol., 66, pp. 656-659, 1980.
Gonzalez-Carranza et al., Temporal and Spatial Expression of a Polygalacturonase during Leaf and Flower Abscission in Oilseed Rape and Arabidopsis, Plant Physiology, 128, pp. 534-543, Feb. 2002.
Hay et al., A Bioluminescent Whole-Cell Reporter for Detection of 2, 4-Dichlorophenoxyacetic Acid and 2,4-Dichlorophenol in Soil, Applied and Environmental Microbiology, pp. 4589-4594, Oct. 2000.
Hetherington et al., The absorption, translocation and distribution of the herbicide glyphosate in maize expressing the CP-4 transgene, Journal of Experimental Botany, 50(339), pp. 1567-1576, Oct. 1999.
Hollis et al., Design and Application of a Biosensor for Monitoring Toxicity of Compounds to Eukaryotes, Applied and Environmental Microbiology, pp. 1676-1679, Apr. 2000.
Idahl et al., Measurements of Serum Glucose Using the Luciferin/Luciferase System and a Liquid Scintillation Spectrometer, Analytical Biochemistry, 155, pp. 177-181, 1986.
Lager et al., Conversion of a Putative Agrobacterium Sugar-binding Protein into a FRET Sensor with High Selectivity for Sucrose, The Journal of Biological Chemistry, 281(41), pp. 30875-30883, Oct. 13, 2006.
Mourad et al., Measurement of Oxidized Glutathione by Enzymatic Recycling Coupled to Bioluminescent Detection, Analytical Biochemistry 283, pp. 146-152, 2000.
Mueller-Klieser et al., Geographical mapping of metabolites in biological tissue with quantitative bioluminescence and single photon imaging, Histochemical Journal, 25, pp. 407-420, 1993.
Oldham et al., Three-dimensional imaging of xenograft tumors using optical computed and emission tomography, Med Phys., 33(9), pp. 3193-3202, Sep. 2006.
Sattler et al., A bioluminescence technique for quantitative and structure-associated imaging of pyruvate, Laboratory Investigation, 87, pp. 84-92, 2007.
Servaites et al., Glyphosate Effects on Carbon Assimilation, Ribulose Bisphosphate Carboxylase Activity, and Metabolite Levels in Sugar Beet Leaves, Plant Physiol, (1987) 85, pp. 370-374.
Shao et al., Novel Cyanobacterial Biosensor for Detection of Herbicides, Applied and Environmental Microbiology, 68(10), pp. 5026-5033, Oct., 2002.
Smulski et al., Combined, Functional Genomic-Biochemical Approach to Intermediary Metabolism: Interaction of Acivicin, a Glutamine Amidotransferase Inhibitor, with *Escherichia coli* K-12, Journal of Bacteriology, pp. 3353-3364, Jun. 2001.

* cited by examiner

*Primary Examiner* — Kagnew H Gebreyesus
(74) *Attorney, Agent, or Firm* — James E. Davis; Joseph A. Schaper; Harness, Dickey & Pierce, P.L.C.

(57) ABSTRACT

Methods and compositions are provided for spatial imaging and quantifying glyphosate in plant tissue. Glyphosate oxidoreductase is coupled to a cycling flavin mononucleotide-oxidoreductase-luciferase system. The resulting bioluminescence is proportional to the amount of glyphosate, allowing glyphosate to be observed within plant tissue and quantified.

20 Claims, 11 Drawing Sheets

IMAGING GLYPHOSATE IN PLANT TISSUE

CROSS-REFERENCE TO RELATED APPLICATIONS

This application is a U.S. national stage filing under 35 U.S.C. §371 of International Application No. PCT/US2010/026673 filed Mar. 9, 2010, which published as WO 2010/104861 on Sep. 16, 2010, and which claims the benefit of and priority to U.S. Provisional Application No. 61/158,840, filed on Mar. 10, 2009. The entire disclosures of each of the above applications are incorporated herein by reference.

INTRODUCTION

The compound N-(phosphonomethyl)glycine, commonly referred to as glyphosate, is a foliar applied, broad spectrum, post-emergence herbicide used for controlling annual and perennial grasses as well as dicotyledonous plants. Advantageous features of glyphosate include rapid soil inactivation and degradation with low toxicity to non-plant organisms. A mode of action of glyphosate includes inhibition of 5-enolpyruvyl shikimate 3-phosphate synthase (EPSP synthase), a key enzyme in the shikimate pathway, which is required for the biosynthesis of aromatic compounds including aromatic amino acids, vitamins, plant growth substances, and lignin. In particular, inhibition of EPSP synthase by glyphosate prevents the conversion of phosphoenolpyruvic acid and 3-phosphoshikimic acid to 5-enolpyruvyl-3-phosphoshikimic acid.

Glyphosate's herbicidal activity is generally nonselective; however, this may be overcome by genetically selecting and/or genetically engineering a plant to increase its resistance to the herbicide. A genetically selected or engineered plant of interest may be cultivated in the presence of glyphosate while growth of competitive plants is suppressed by the herbicide. Herbicide-tolerant plants may also reduce the need for tillage to control undesired plants, thereby effectively reducing soil erosion. Glyphosate-tolerant plants may be produced by modifying the plant DNA to produce or increase the activity of an EPSP synthase that is glyphosate tolerant. Alternatively, expressing genes capable of glyphosate degradation can provide a means of conferring glyphosate tolerance to plants or can augment the tolerance of transgenic plants already expressing a glyphosate tolerant EPSP synthase, depending upon the physiological effects of the degradation products.

Glyphosate metabolism and breakdown may generate the compound aminomethylphosphonate (AMPA). Breakdown of glyphosate may be accomplished by the plant or by microbes on the leaf surface to which glyphosate is applied. In some cases, AMPA may be less phytotoxic as compared to glyphosate.

The enzyme glyphosate oxidoreductase (GOX) catalyzes the cleavage of the C—N bond of glyphosate yielding aminomethylphosphonate (AMPA) and glyoxylate as the reaction products. Under aerobic conditions, oxygen can be utilized as a co-substrate for the reaction. Other electron carriers such as phenazine methosulfate and ubiquinone may stimulate the reaction under aerobic conditions. In the absence of oxygen, these compounds can act as electron acceptors. Glyphosate oxidoreductase and expression thereof is described in U.S. Pat. Nos. RE38,825 to Barry et al.; U.S. Pat. No. 6,849,430 to Carson et al.; U.S. Pat. No. 5,463,175 to Barry et al.; and U.S. Pat. No. 5,776,760 to Barry et al.

Various methods may be used to assay the activity of GOX, as described in U.S. Pat. No. RE38,825 to Barry et al. In one method, the enzymatic reaction may be assayed by oxygen uptake using an oxygen electrode. In another method, reaction of a sample containing glyphosate with 2,4-dinitrophenylhydrazine can form glyoxylate-2,4-dinitrophenylhydrazone, where the amount of this product is determined using HPLC analysis. In yet another method, [3-$^{14}$C]-glyphosate may be used as a substrate and the radioactive AMPA produced by the enzyme separated from the substrate using HPLC with an ion-exchange column. The radioactive AMPA is a measure of the extent of the glyphosate oxidoreductase reaction. These methods, however, do not detect or quantitate glyphosate or enzymatic reactions linked to glyphosate in situ.

SUMMARY

The present invention provides compositions and methods for imaging and measuring the distribution of glyphosate in plant tissue.

In some embodiments, the present disclosure relates to a method for imaging and quantifying glyphosate in plant tissue expressing glyphosate oxidoreductase (GOX). The method includes contacting plant tissue with an enzyme cocktail, the enzyme cocktail comprising oxidized nicotinamide adenine dinucleotide phosphate (NADP+), flavin mononucleotide (FMN), flavin oxidoreductase, a long-chain fatty aldehyde, and luciferase. The method also includes measuring light emission from the plant tissue, wherein light emission is proportional to glyphosate in the plant tissue.

In some embodiments, the present disclosure relates to a method for imaging and quantifying glyphosate in plant tissue. Plant tissue is contacted with an enzyme cocktail, the enzyme cocktail comprising oxidized nicotinamide adenine dinucleotide phosphate (NADP+), glyphosate oxidoreductase (GOX), flavin mononucleotide (FMN), flavin oxidoreductase, a long-chain fatty aldehyde, and luciferase. Light emission from the plant tissue is measured, wherein light emission is proportional to glyphosate in the plant tissue.

The present methods may include various additional features. For example, cellular enzymes in the plant tissue may be inactivated by heating prior to the contacting. Reduced nucleotides in the plant tissue may be selectively removed by acid treatment prior to the contacting, the acid treatment comprising treating the plant tissue with acid and neutralizing the acid. The acid treatment may include treating the plant tissue with HCl and ascorbic acid, adding additional HCl to the plant tissue, and neutralizing the plant tissue with NaOH and $K_2HPO_4$. Measuring light emission from the plant tissue may further comprise measuring light emission throughout a discrete time interval. Measuring light emission from the plant tissue may also further comprise recording an image of the light emitted from the plant tissue.

The present methods may be used to compare light emission from various plant tissue samples, including those from the same individual plant, same species, different species, and/or genetically modified or non-modified plants. The methods may also be used to visualize glyphosate in microorganisms, fungi, or isolated cell organelles. The methods may also include comparison with various controls, including comparing light emitted from the plant tissue to light emitted from at least one known amount of glyphosate mixed with the enzyme cocktail.

In some embodiments, the present disclosure relates to a kit for quantifying glyphosate in plant tissue. The kit includes oxidized nicotinamide adenine dinucleotide phosphate (NADP+); glyphosate oxidoreductase (GOX); flavin mononucleotide (FMN); flavin oxidoreductase; a long-chain fatty aldehyde; and luciferase. The kit may further include glyphosate which may be used as a control. In some cases, the glyphosate oxidoreductase (GOX) is packaged separately from the other components. For example, this allows the other components to be used with plant tissue expressing glyphosate oxidoreductase (GOX) without the addition of exogenous glyphosate oxidoreductase (GOX).

To further understand the dynamics of glyphosate and plant biology, the present disclosure provides advantages for assaying glyphosate in vivo and allows observation and quantitation of the distribution of glyphosate and enzymes linked to glyphosate within plant tissue.

"A" and "an" as used herein indicate "at least one" of the item is present; a plurality of such items may be present, when possible. "About" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters. In addition, disclosure of ranges includes disclosure of all distinct values and further divided ranges within the entire range.

DRAWINGS

Certain aspects of the present invention will be more fully understood from the detailed description and the accompanying drawings, in which.

The drawings described herein are for illustration purposes only and are not intended to limit the scope of the present disclosure in any way.

DETAILED DESCRIPTION

Further areas of applicability and advantages will become apparent from the following description. It should be understood that the description and specific examples, while exemplifying various embodiments of the invention, are intended for purposes of illustration and are not intended to limit the scope of the invention.

The present invention provides compositions, methods, and systems for spatially imaging glyphosate within plant tissue, including cells and organelles of plant tissue, and microorganisms. Plant tissue of interest may be sectioned and applied to microscope slides whereupon an enzyme cocktail is applied to the tissue to provide a bioluminescence reaction. Light detection and quantitation correlates with the amount of glyphosate within the plant tissue. Imaging may be used to ascertain the distribution of glyphosate within the plant tissue at cellular and/or subcellular levels. Quantitative methods may be used to determine glyphosate concentrations relative to tissue volume.

Figure 1:
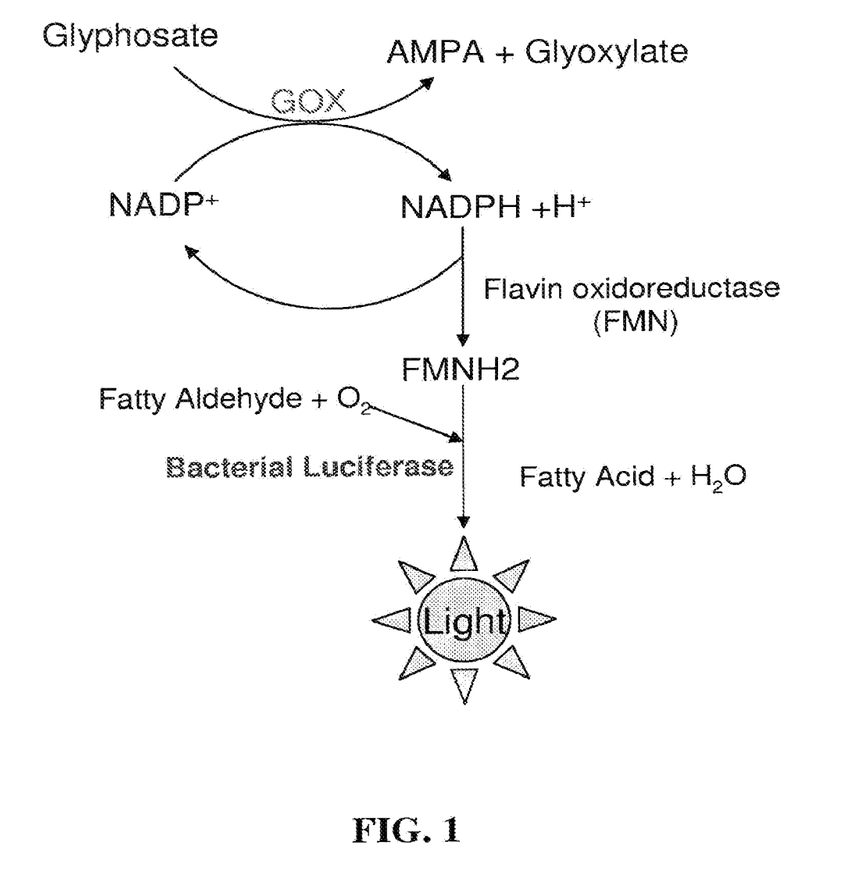
FIG. 1 illustrates a cycling FMN-oxidoreductase-luciferase system where detection of glyphosate is via bioluminescence.

In some embodiments, the present disclosure provides analytical imaging methods for the detection and quantitation of glyphosate in plant tissues. These methods may be based on enzymatic reactions that link glyphosate to luciferase with subsequent light emission. These methods may include linking the generation of reaction products and (NADPH$^+$ and H$^+$) to a luciferase assay in a solution that can be applied to frozen sections of live tissues. The production of NADPH$^+$ and H$^+$ is obtained following the enzymatic conversion of glyphosate to aminomethylphosphonate (AMPA) and glyoxylate by the glyphosate oxidoreductase (GOX) enzyme, as shown in FIG. 1. Location of glyphosate may then be detected and quantified in real time using fluorescence microscopy, including confocal, multispectral, and hyperspectral microscopy. Other microscopic imaging approaches, such as those utilizing quantum dots and other fluorescent labels or fluorophores, may also be employed as additional tools for illuminating and detecting one or more chemical reaction sites.

With reference to FIG. 1, an embodiment of a cycling FMN-oxidoreductase-luciferase system is shown, where detection of glyphosate is via bioluminescence. The biochemical method is based on luminescence produced by luciferase, for example bacterial luciferase derived from *Photobacterium fischeri*. Glyphosate is linked to a nicotinamide adenine dinucleotide phosphate redox system (NADP/NADPH+H$^+$) through specific enzymes, and the redox system is connected to bacterial luciferase via flavin oxidoreductase. Using this system, the amount of glyphosate can be linked quantitatively through the flux of linked enzyme reaction products to the amount of light generated. Glyphosate oxidoreductase (GOX), shown in FIG. 1, catalyzes the formation of AMPA and glyoxylate from glyphosate by converting the electron acceptor NADP$^+$ to its reduced form, NADPH. Flavin oxidoreductase uses NADPH, H$^+$, and flavin mononucleotide (FMN) to catalyze the formation of FMNH$_2$ and NADP$^+$. Luciferase catalyzes the bioluminescent oxidation of FMNH$_2$ and a long-chain aliphatic aldehyde, such as decanal, to produce FMN, the corresponding long-chain fatty acid, and water. In this process, emission of light is proportional to the initial glyphosate concentration.

In some embodiments, the present systems and methods may also be used to measure amount and distribution of pyruvate, lactate, ATP, and glucose within tissue, cells, organelles, and microorganisms. In addition, other examples of long chain aldehydes suitable for luciferase assays include aliphatic aldehydes such as heptanal, octanal, nonanal, undecanal, etc. In some embodiments, flavin oxidoreductase may be used. Other luciferase enzymes that may be used include click beetle, deep-sea squid, etc. that can result in yellow, red, green, and orange-emitting light reactions. In addition, there are other luciferin substrates (adenylate substrates) that can provide different color light emitters. Likewise, several luciferases mutants have been produced to give different light emitter colors. One or more different colored light emitters may be employed in a single cocktail for simultaneous detection of different analytes (e.g., glyphosate plus ATP, sucrose, lactate or other NADP(H) dependent reactions) by using combinations of luciferases and/or luciferase substrates. Simultaneous imaging assays may also be used to measure and/or localize energy metabolites (ATP, citrate, glucose, lactate, pyruvate, etc) and thus help elucidate the effect of glyphosate in plant health and physiology. For example, this may be accomplished by using a cocktail that includes enzymes and/or substrates yielding two or more different light colors (e.g., green/red, green/yellow, etc).

Certain additional compounds may also be included in the present luciferase cocktail, such as coenzyme A, BSA, neutral detergents, and cytidine nucleotides (CTP, dCTP, dCDP, etc.). These compounds alone or in combination can lead to an amplification of the light signal and thereby enhance the signal of transient or non-abundant analytes of interest in plants, for example, by increasing sensitivity of the assay.

Bioluminescence generated by luciferase therefore allows indirect visualization of the spatial distribution of glyphosate in plant tissues by single and/or two-photon microscopy. The cycling FMN-oxidoreductase-luciferase system may be used to measure glyphosate within plant tissue sections, cells, or organelles.

In some embodiments, methods include contacting glyphosate-treated plant tissue sections with a luciferase enzyme and reagent cocktail where subsequent light emission is indicative of the presence and quantity of glyphosate. The associated enzymatic reactions and resulting light emission produce a signal distribution across the cryosection with intensity proportional to the glyphosate concentration. The emitted light may be visualized through a microscope and/or an imaging microscope/scanner, and the respective image can be transferred to a computer for image analysis. In various embodiments, the emitted light may be measured by using one or more of a microscope, scanner, plate reader, spectrofluorometer, and a hyperspectral imager. A combination of one or more calibration procedures and a confocal microscope allows the quantitative calculation of regional glyphosate within tissue sections.

In some embodiments, the cycling FMN-oxidoreductase-luciferase system may be coupled to other target compounds, where a reaction involving the target compound (e.g., requiring a dehydrogenase) can be linked to the FMN-oxidoreductase-luciferase system. For example, various metabolites or proteins may be detected by these methods, where turnover of the metabolite or protein either directly or indirectly feeds into the NADP/NADPH+H$^+$ and/or FMN/FMNH$_2$ cycles depicted in FIG. 1.

In some embodiments, detection and quantitation of glyphosate may further include the following features. In order to obtain more consistent results in the determination of glyphosate for standard, control, and unknown tissue sections, cellular enzymes in the cryosection may be inactivated by heating at about 100° C. for about 10 min. The light intensity of the bioluminescence reaction may be calibrated in absolute terms using homogenates of the heat-inactivated tissue which may be exposed to a solution with different glyphosate concentrations to provide a standard curve, for example. A combination of the calibration procedure and confocal microscope allows the quantitative calculation of regional glyphosate within the tissue sections in conjunction with measurements of the glyphosate control reactions.

Concentration values in µmoles/g with regard to tissue volume may be determined by comparing the bioluminescence intensity of the respective tissue sections with that of the standard sections. To prepare standard sections of about 20 µm, tissue callus may be treated with different glyphosate concentrations in the range of 0-200 mM. The angle and positioning of the tissue sections for analysis may be set in a consistent and uniform manner in order to minimize error in measurements. In this way, the difference between concentrations of glyphosate will not come from different angles of tissue sections.

Cryosections may be adhered to the upper side of a cover glass that is laid upside down upon a glass slide with a rectangular casting-mold. The mold is filled with a liquid reaction solution containing an enzymatic cocktail (see Table 1) that links glyphosate cleavage by glyphosate oxidoreductase (GOX) via the NADP+/NADPH+H$^+$ redox system to the FMN-oxidoreductase-luciferase light reaction. Enzymes and coenzymes in the cocktail may be obtained from commercial suppliers. Spatial distribution of bioluminescence within the tissue section is monitored following tissue contact with the enzymatic reaction mix using a microscope (e.g., Zeiss) and an imaging photon counting system. The photon intensity is integrated over about 90 sec, beginning about 10 sec after the light-emission by luciferase reaction is started. The casting mold carrying the tissue section under the microscope is held in a temperature controlled environment in order to make the kinetics of the enzyme reactions more reproducible. Digitized images of the glyphosate distributions are processed using image analysis software.

TABLE 1

Constituents of enzyme cocktail for the detection of glyphosate via bioluminescence.

| Reagent | Concentration |
| --- | --- |
| MOPS | 100 mM |
| Tricine | 10 mM |
| NADP$^+$ (FAD) | 75 mM |
| MgCl$_2$ | 10 mM |
| GOX enzyme | 42 mg/ml |
| FMN | 0.4 mM |
| Decanal | 8 mM |
| 1,4-dithiothreitol | 0.5 mM |
| Luciferase | 0.13 Units/ml |
| NAD(P)H-FMN Oxidoreductase | 8 Units/ml |

The enzyme cocktail allows for sensitive detection of even low amounts of glyphosate as well as assessment of its spatial distribution on a microscopic level in relation to the tissue structure.

In some embodiments, bioluminescence measurement includes the following methods and compositions. For bioluminescence imaging, coverglasses with adhered cryosections of standards, reference samples, or tissue are laid upside down on a metal slide with a casting mold. The mold is filled with the enzyme cocktail (Table 1). The tissue section is positioned in a way so that it is in close contact with the solution. This sandwich is transferred immediately to a temperature-controlled reaction chamber on the stage of an appropriate microscope (e.g., Axiophot, Zeiss, Oberkochen, Germany). After a 10 sec incubation time at 30±1° C., bioluminescence is collected for a defined time interval. Emission of light is detected with a 16-bit CCD camera coupled to an imaging photon counting system (e.g., C2400, Hamamatsu, Herrsching, Germany) that is connected to the microscope. The whole assembly is located within a light-tight black box to prevent registration of background photons from the environment.

In some embodiments, bioluminescence measurement includes the following methods and compositions. A cryosection of plant tissue is obtained and incubated for 10 min at 100° C. to heat inactivate cellular enzymes. The cryosection is refrozen and adhered to a glass slide. The glass slide is laid upside down so that the cryosection contacts a chamber containing frozen enzyme cocktail, such as that shown in Table 1. The temperature of the chamber is heated above the melting point of the enzyme cocktail to start the luciferase reaction. Spatial distribution of the bioluminescence intensity within the tissue section is measured directly using a microscope and imaging photon-counting system. Adjacent cyrosections may also be imaged using visible light and/or various stains to help orient the bioluminescence images with respect to the plant tissue structure, including cellular structures and/or subcellular structures.

Figure 2:
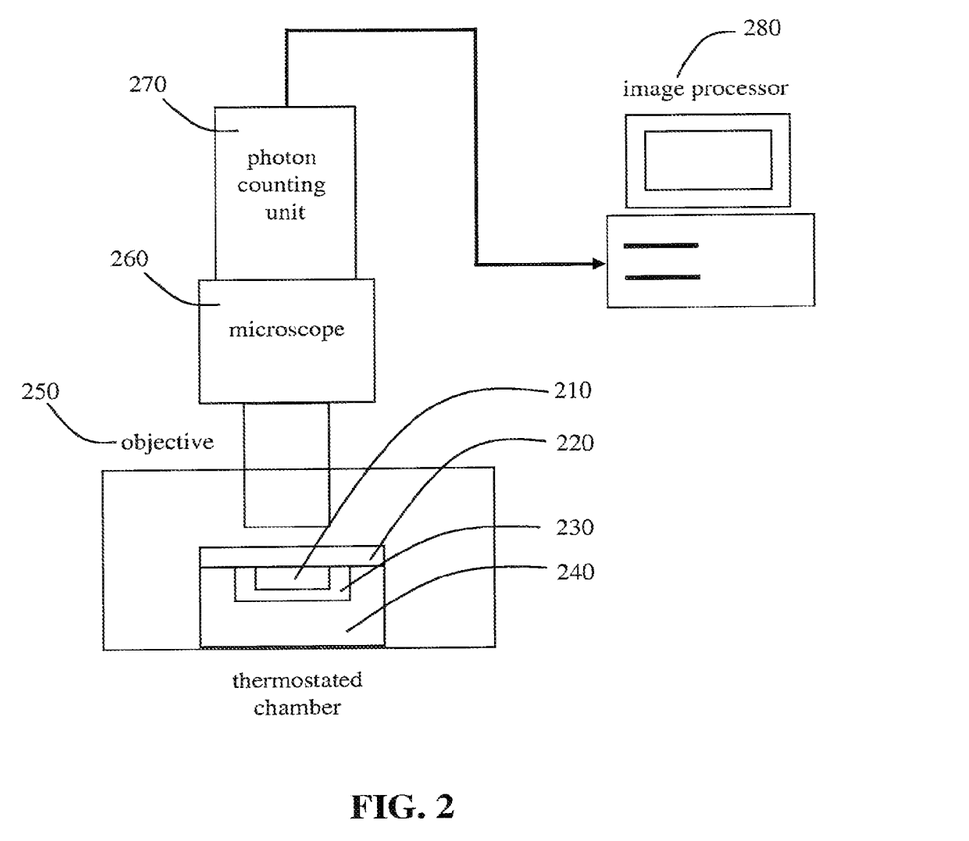
FIG. 2 illustrates an embodiment of a system for high-resolution single-photon imaging and quantitative bioluminescence in plant tissues constructed according to the present disclosure.

With reference to FIG. 2, an embodiment of an experimental setup constructed in accordance with the present disclosure is shown. The system provides high-resolution single-photon imaging and quantitative bioluminescence in plant tissues. The tissue section 210 is applied to a cover glass 220 that is inverted to contact the tissue section 210 with an enzyme cocktail 230 contained within a temperature-controlled chamber 240. The tissue section 210 image is sent through an objective 250 of a microscope 260 to a photon counting unit 270 that converts the image into a digital signal for receipt by an image processor 280. The image processor 280 is used to determine the position and intensity of the bioluminescent signal over a time interval.

In some embodiments, the experimental setup may include a confocal microscope, such as a Zeiss LSM510 META confocal microscope, which may be used with a two-photon laser, where the chamber is not thermostated.

The resulting bioluminescence images of plant tissue standards, controls, and unknown samples may be analyzed using Wasabi imaging software (Hamamatsu Photonic Systems Corp., Bridgewater, N.J.) and Origin data and graphic analysis software (OriginLab Corporation, Northampton, Mass.). Images of the spatial distribution of light intensities in tissue sections may be overlaid with other images, such as chlorophyll autofluorescence. Photoshop (Adobe Systems Incorporated, San Jose, Calif., USA), ImageJ (National Institutes of Health, Bethesda, Md.), Excel (Microsoft, Redmond, Wash., USA) and other similar software may be used for quantitation and evaluation of bioluminescence images. In some embodiments, the glyphosate-dependent bioluminescence assay and the intensity of light may be dependent not just on the concentration within the section but also on the section thickness. Thus, it may be important to prepare and use cryosections of identical thickness throughout measurement and calibration.

Figure 3:
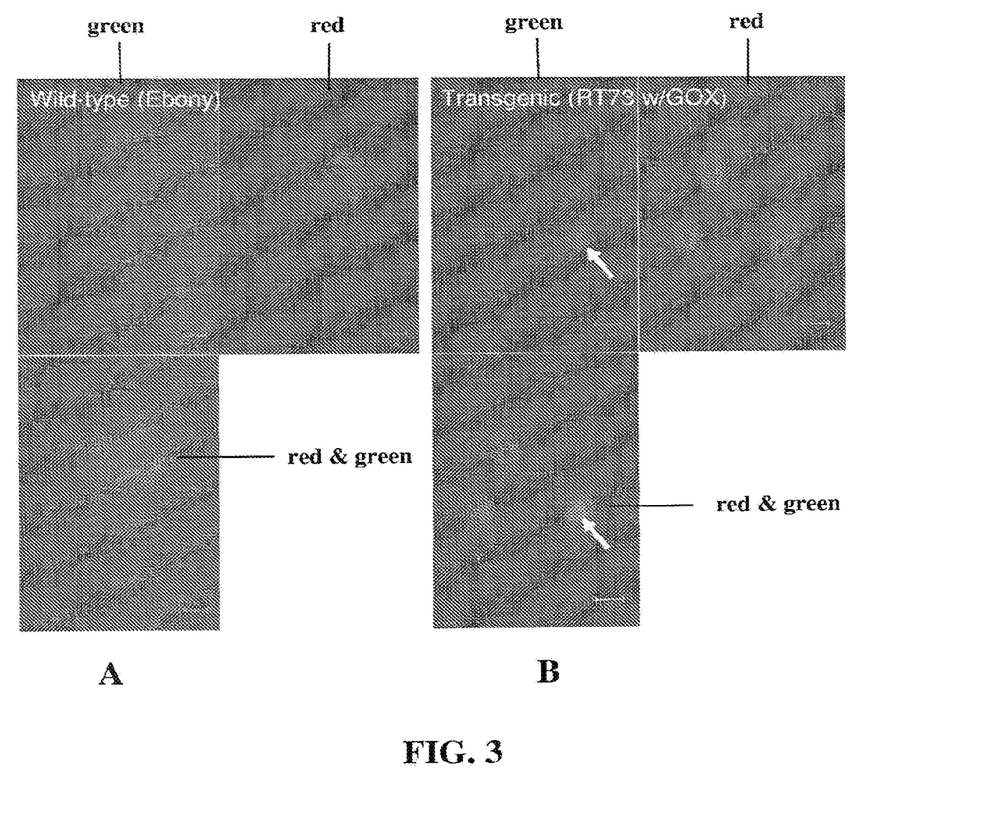
FIG. 3 illustrates in vivo glyphosate visualization in leaf cells of canola plants expressing GOX, where light emission (indicated by arrows) is only detected in chloroplasts of transgenic leaves after 15 min incubation in the cocktail mix.

Referring now to FIG. 3, bioluminescence images are shown that illustrate in vivo glyphosate visualization in leaf cells of canola plants expressing GOX. Panel (a) shows images of the Ebony cultivar of canola as wild-type plants and panel (b) shows images of transgenic RT73 canola expressing GOX. Light emission via bioluminescence, indicated by arrows in panel (b), is detected after 15 min incubation in the cocktail mix only in the chloroplasts of the transgenic plant leaves.

In some embodiments, glyphosate detection and quantitation methods may be applied to plant tissues that do not express glyphosate oxidoreductase (GOX). For example, GOX may be extracted and/or purified from a plant expressing the GOX enzyme or from a recombinant source. Addition of GOX to the enzyme cocktail can therefore extend the glyphosate detection method to plant samples without endogenous GOX. For example, enzyme cocktail including GOX may be used for spatial imaging and quantitation of glyphosate that is applied to any plant, for example, undesired plants such as weeds, in order to measure glyphosate amounts and distribution through the plant's tissue. GOX and/or the enzyme cocktail including GOX may be part of a kit to detect and quantify glyphosate in any plant, both in vivo and in vitro. These methods may also be coupled with other tools, markers, and probes and may be used to screen explants.

Evaluation and variation of methods for the spatial imaging and quantitation of glyphosate may include the following additional features. Glyphosate may be visualized in canola leaves expressing GOX following incubation in a cocktail staining mix. Light emission is a result of glyphosate conversion to AMPA and glyoxylate by GOX. The bioluminescence is dependent on GOX activity and does not originate from a secondary source or an alternative reaction in the cells.

Figure 4:
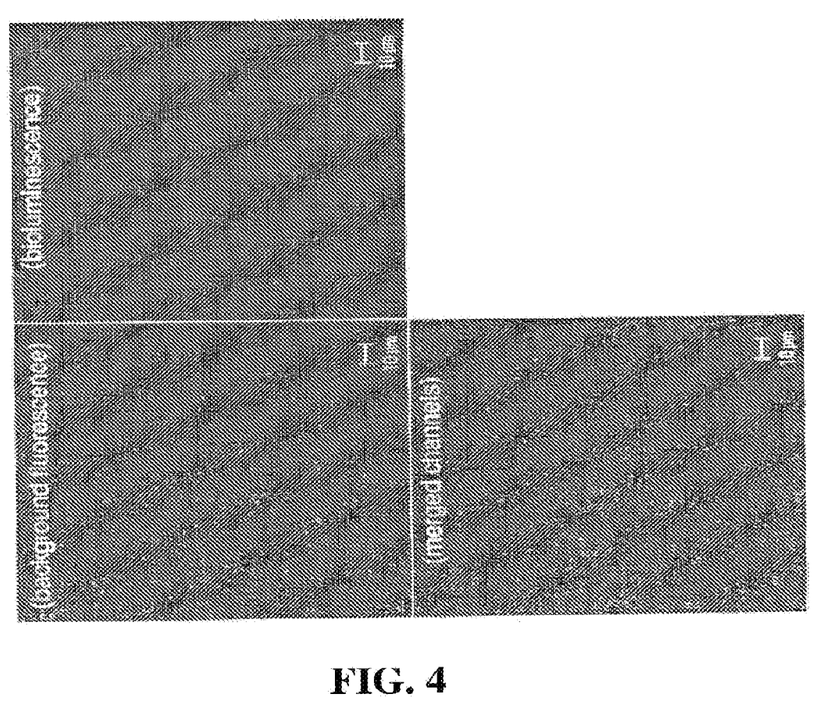
FIG. 4 illustrates digital images obtained after linear unmixing using spectra collected for pollen autofluorescence and bioluminescence, where absence of an image on the bioluminescence channel (top right panel) indicates that no light emission is detected that matched that particular spectrum.

In order to establish that the origin of the light is dependent on the presence of glyphosate in the cells, the present methods and compositions are applied to pollen from RT73 canola plants instead of the leaves. Using enzyme cocktail containing no GOX, multi-photon image acquisition and analysis shows that no light emission is detected for RT73 pollen grains following incubation in the cocktail mix with and without glyphosate. Linear unmixing, using spectra previously collected, further confirms that the detected signal is originating from fluorescent compounds and not bioluminescence, as shown in FIG. 4. Since RT73 pollen grains do not express GOX, these results demonstrate that the indirect glyphosate detection method using enzyme cocktail is not influenced by a secondary source or alternative reaction.

The effect of increasing concentrations of glyphosate on light emission may be evaluated using the following methods and compositions. Hand-made sections of RT73 (GOX expressing) and Ebony (wild-type) canola leaves are incubated in cocktail mixtures containing the following concentrations of glyphosate: 0, 2.5, 5, 10, 15, 20, and 30 mM. Incubation is performed directly on a slide in a drop of cocktail mix (about 20 to 100 µL, or another volume that covers the tissue sample) and images are acquired from thereon; alternatively, the samples are incubated in wells (about 100-300 µL, or any other volume that covers the sample) for about 45 min and then transferred to slides for image acquisition. Slides may be replaced by any support that allows light capture from any direction. Other time intervals for incubation and/or observation are tested, such as from about 5 min to 180 min. For RT73 samples incubated on slides, light emission is captured 5 to 10 min after incubation in the cocktail mixture for concentrations of glyphosate equal or above 10 mM; and after 30 min, for cocktail mixtures with 5 mM glyphosate. For samples incubated in wells for about 45 min prior to observation, light emission is detected for all concentrations, increasing with the increase of glyphosate present in the cocktail mixture. For wild-type canola samples (Ebony), no change on light emission was detected for any of the samples, as shown in FIG. 5 and FIG. 6.

Figure 5:
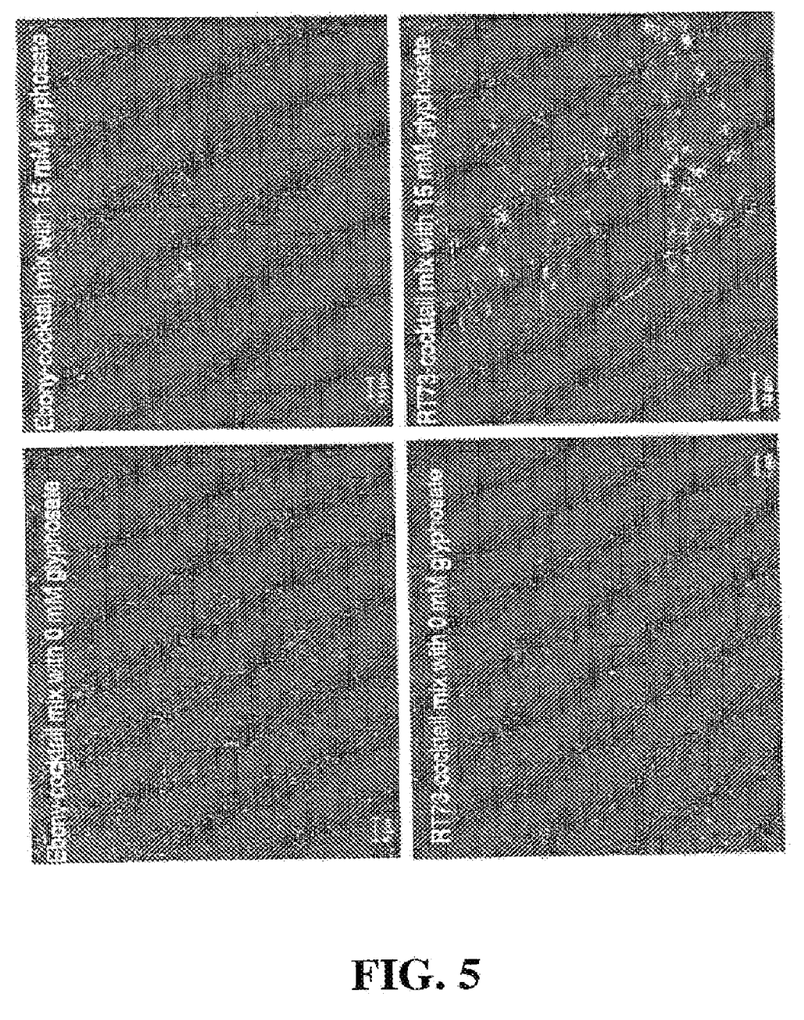
FIG. 5 illustrates confocal images from wild-type (Ebony) and GOX expressing (RT73) canola leaf cells after incubation in a cocktail mixture without glyphosate (0 mM) or with 15 mM glyphosate.

FIG. 5 shows confocal images from wild-type (Ebony) and GOX expressing (RT73) canola leaf cells after incubation in a cocktail mixture without glyphosate (0 mM) or with 15 mM glyphosate. Red fluorescence indicates the presence of chlorophyll in the leaf chloroplasts, while green (bioluminescence) indicates the presence of glyphosate indirectly detected by the enzymatic reaction that links glyphosate oxidation by glyphosate oxidoreductase (GOX) to a cycling system with FMN-oxidoreductase-luciferase. No light emission (bioluminescence; green) is detected for Ebony leaf samples incubated in any of the tested cocktail mixtures and glyphosate concentrations. Light emission (bioluminescence; green) is detected for all RT73 samples incubated in cocktail mixtures containing 2.5, 5, 10, 15, 20, and 30 mM glyphosate.

Figure 6:
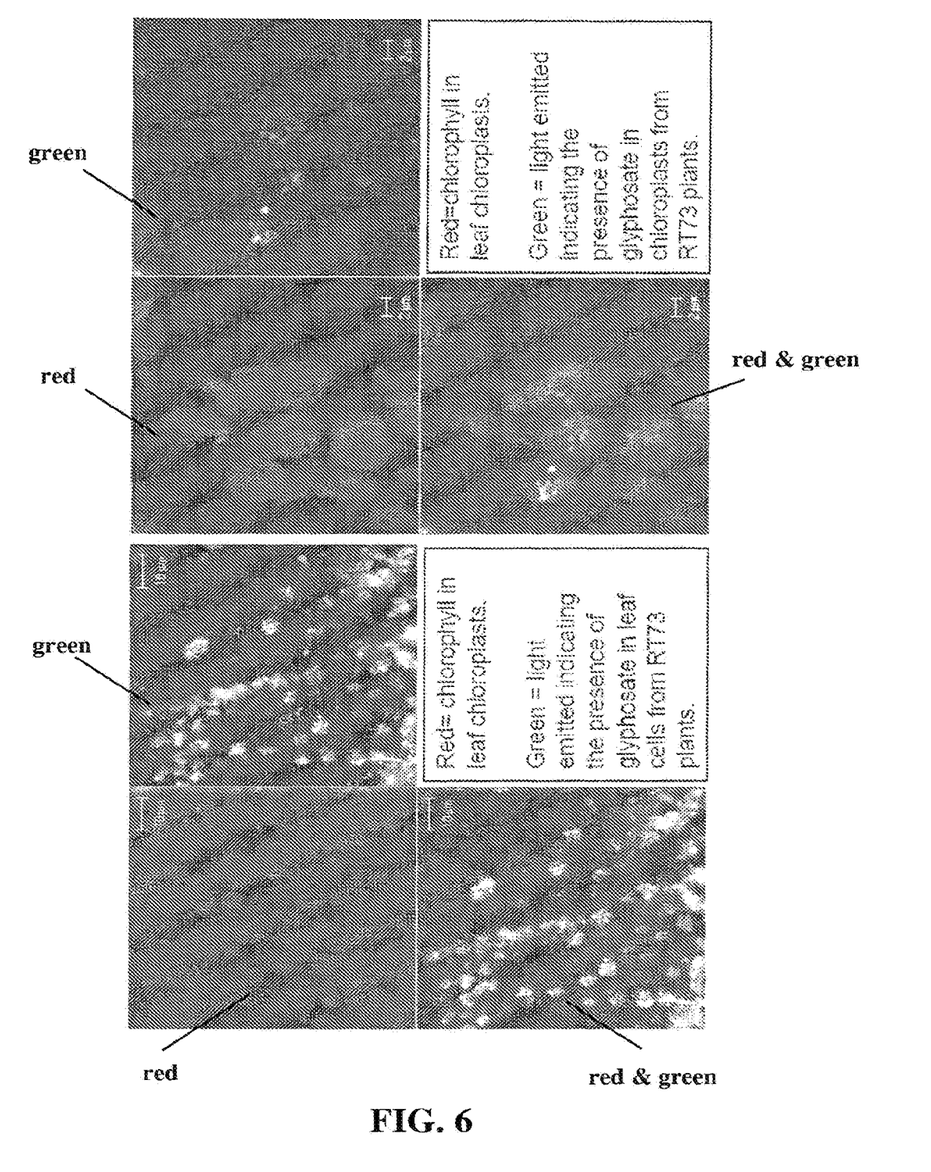
FIG. 6 illustrates confocal images showing the presence of glyphosate (green) in leaf cells and leaf chloroplasts (red) from GOX expressing canola RT73 plants, incubated for 45 min in the cocktail mixture with 5 mM glyphosate.

FIG. 6 includes confocal images showing the presence of glyphosate (green) in leaf cells and leaf chloroplasts (red) from GOX expressing canola RT73 plants, incubated for 45 min in the cocktail mixture with 5 mM glyphosate.

Figure 7:
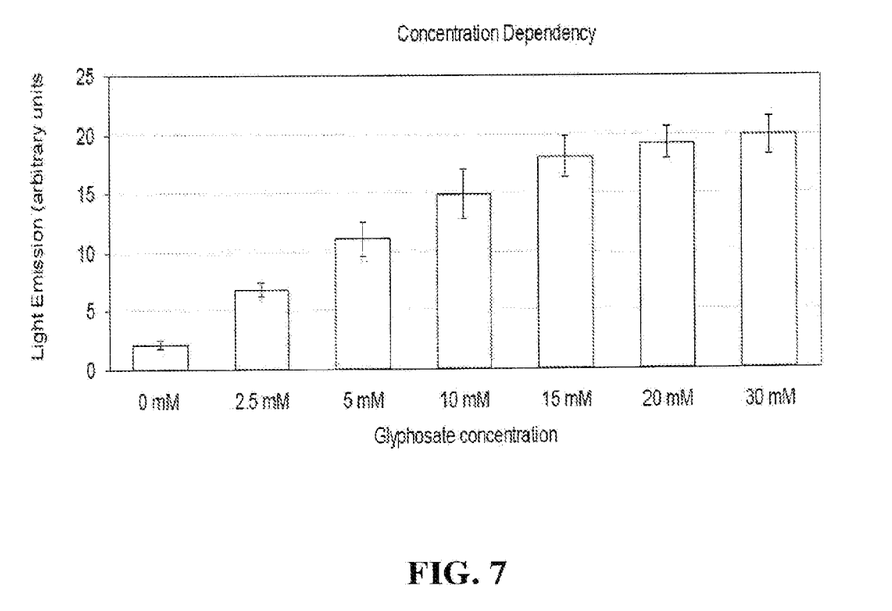
FIG. 7 illustrates an increase in the amount of light detected (bioluminescence) with the increase of glyphosate concentration present in the cocktail mixture.

Analyses include histograms, profiles, and spectra produced from images acquired on the confocal and lambda mode of a Zeiss LSM510 META Two-photon confocal microscope with the Zeiss LSM510 Image Examiner, but other instruments may be used to capture and quantify the light emitted (bioluminescence). The data obtained using the Zeiss software is then transferred to a computer spreadsheet, such as Microsoft Excel, for further analysis. Results confirm that there is a glyphosate concentration dependency relative to bioluminescence. Thus, under the tested conditions, the light emitted increases with increasing glyphosate concentration in the cocktail mixture; example data is shown in FIG. 7.

Figure 8:
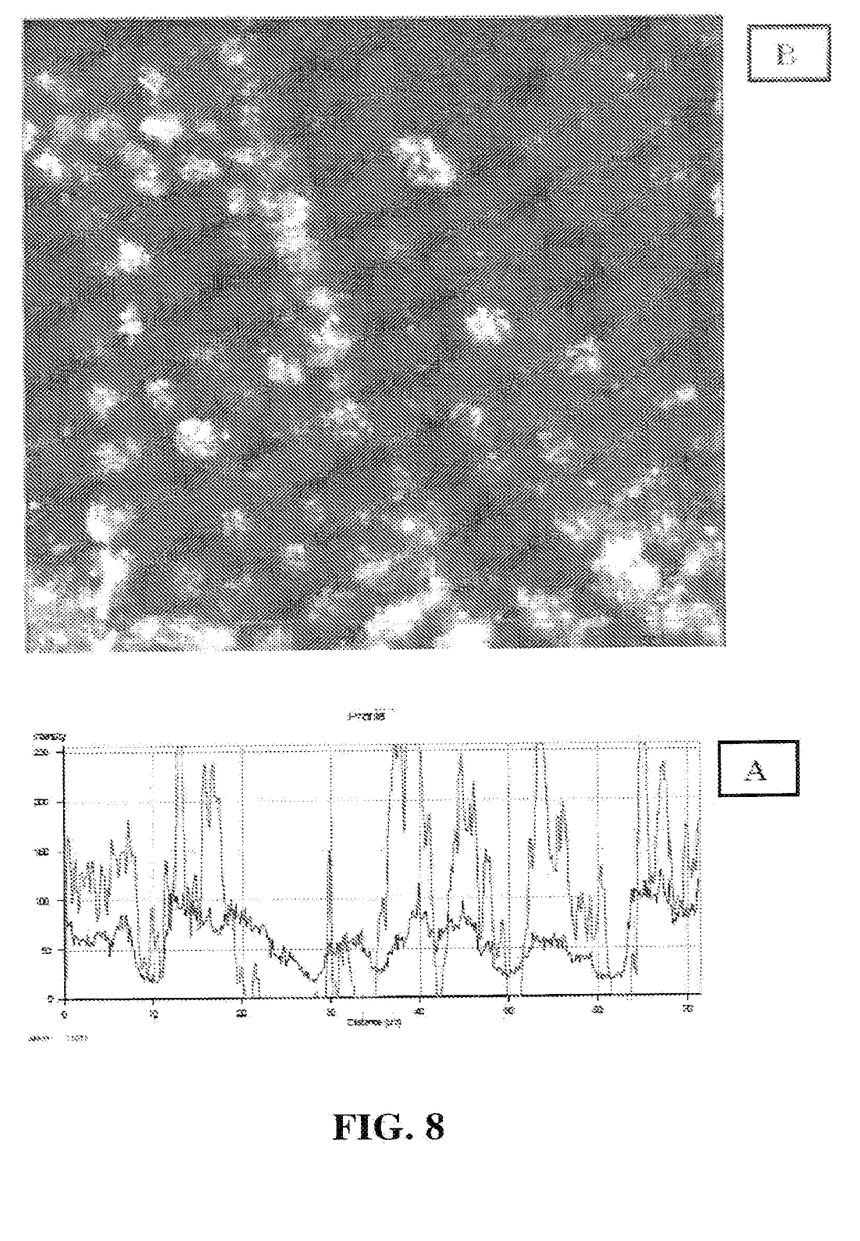
FIG. 8 illustrates profiles (A) for the glyphosate (bioluminescence signal; green) and chlorophyll (red, autofluorescence) obtained from a confocal image (B) of a canola leaf expressing GOX (RT73 plant) after 45 minute incubation in the reaction cocktail mixture containing 5 mM glyphosate.

The light emitted from the sample is captured and visualized on both lambda and confocal modes. The profiles obtained using the confocal mode are produced using large areas of the focal plane, thus capturing profiles from regions where glyphosate and GOX are not present that account, in the profile, for regions of background or very low light emissions, as shown in FIG. 8. Profiles and histograms can be produced for regions where emission is occurring thus avoiding a "dilution effect". Glyphosate is visualized in the chloroplasts and also in the cell cytoplasm. The amount of glyphosate visualized in a particular cell or sample may be affected by the diffusion of the mixture and/or thickness of the sample.

In some embodiments, selective removal of interfering nucleotides (e.g., NADPH to NADH) may be performed as follows. Canola leaf sections from plants expressing GOX (RT73) and wild-type plants (Ebony) are incubated with 20 µL of 0.02 M HCl containing 2 mM ascorbic acid, followed by addition of 90 µL of 0.02 N HCl. After 20 min at RT, the sections are transferred to ice, neutralized with 125 µL of 0.02 M NaOH and 90 µL of 33 mM $K_2HPO_4$, pH 7.0. The sections are then incubated (−NADPH) with enzyme cocktail mixture with 0, 2.5, 5, 10, 1, 20 and 30 mM glyphosate, and observed and analyzed as described. This treatment may selectively destroy the reduced nucleotides forms (NADPH/NADH) while stabilizing the oxidized forms (NADP/NAD+). This can allow the linked reactions to proceed more efficiently in the forward direction (to the luciferase reaction) when NADP+ is included in the luciferase cocktail. Thus, interfering reduced nucleotides (NADPH/NADH) present in the leaf samples may be eliminated and the provided reagent (NADP+) can allow the linked reaction to occur. In this case, NADP+ is provided in addition to the NADP+ formed and/or stabilized in the leaf samples by the acid treatment.

Figure 9:
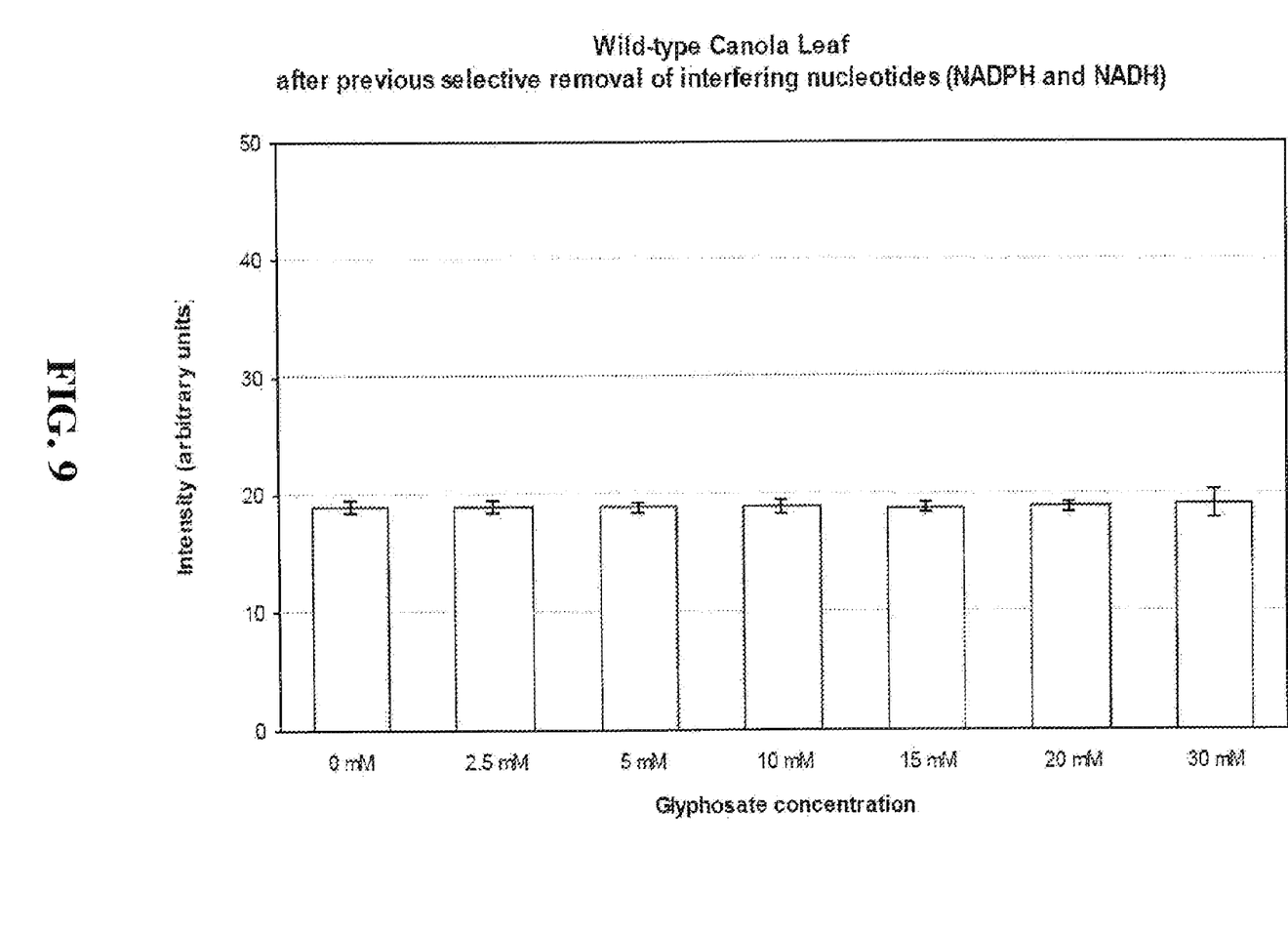
FIG. 9 illustrates Light emission detected for wild-type canola leaf samples incubated in cocktail mixture for 45 minutes after selective removal of interfering nucleotides (NADPH and NADH)
Figure 10:
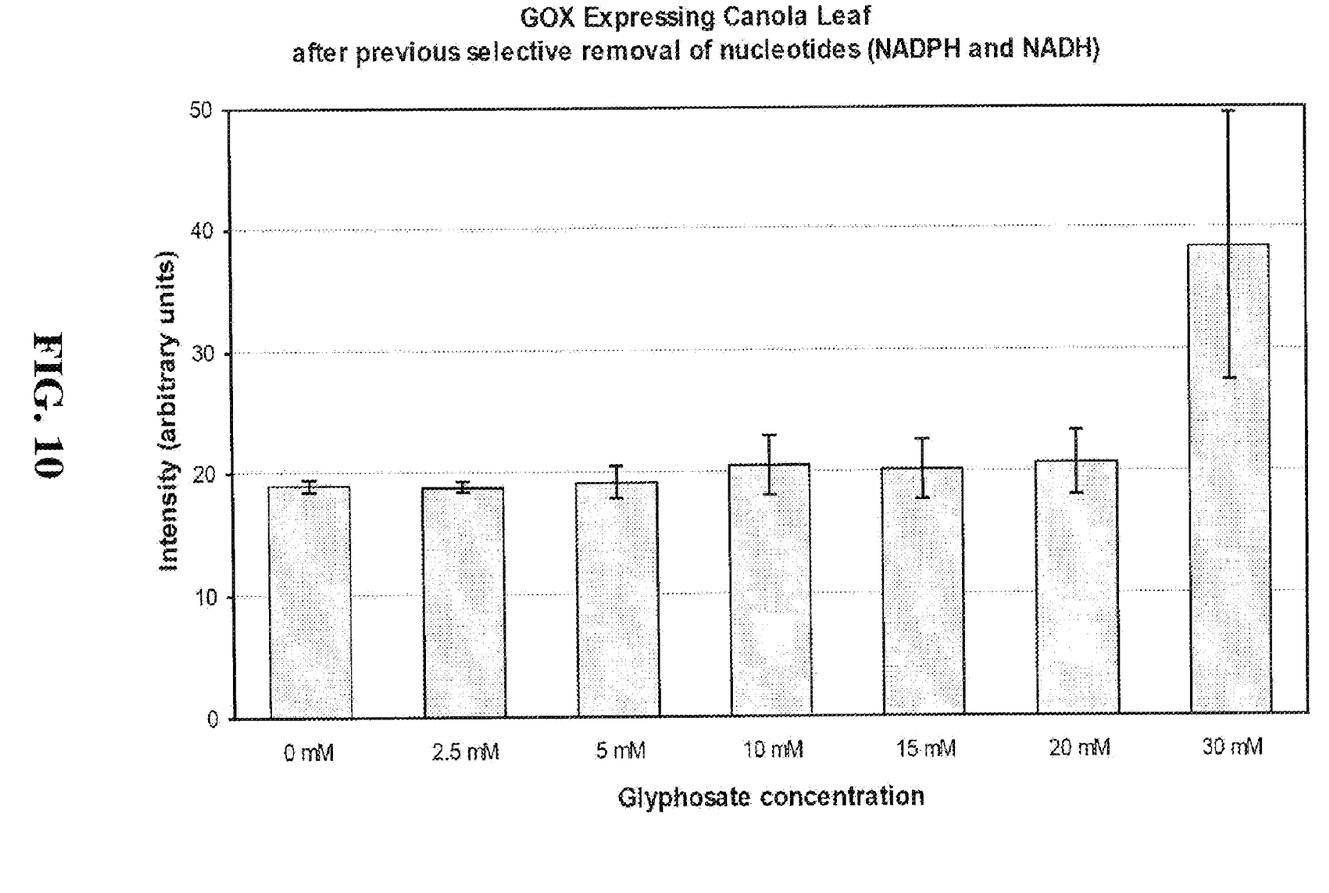
FIG. 10 illustrates light emission detected for GOX expressing canola leaf samples incubated in cocktail mixture for 45 minutes after selective removal of interfering nucleotides (NADPH and NADH)
Figure 11:
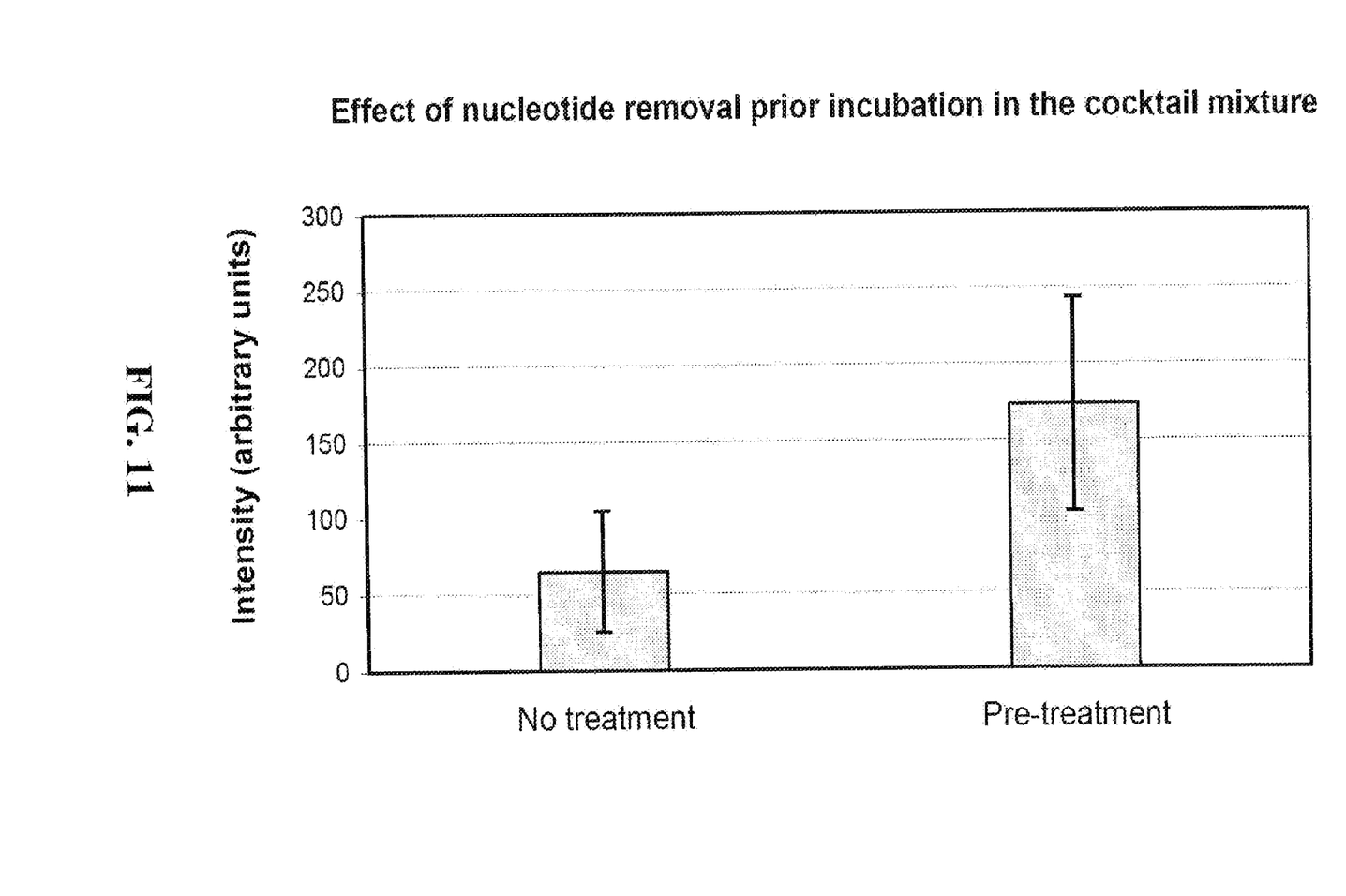
FIG. 11 illustrates light emission detected for GOX expressing canola leaf samples incubated in cocktail mixture with 30 mM glyphosate for 45 minutes without (no treatment) and after (pre-treatment) selective removal of interfering nucleotides (NADPH and NADH).

For wild-type canola leaves, there was no increase in the amount of light emitted (FIG. 9), whereas for GOX expressing canola leaves there was an increase in the amount of light emitted from the samples, which increased with the increase of glyphosate concentration present in the cocktail mixture (FIG. 10). Selective removal of interfering nucleotides such as NADPH and NADH prior incubation of GOX expressing leaf samples in cocktail mixture containing 30 mM glyphosate led to an increase of the signal detected (bioluminescence) when compared to non-treated samples incubated under the same conditions, as shown in FIG. 11.

In some embodiments, glyphosate may be detected in the absence of endogenous GOX. Leaves from sensitive and resistant marestail plants (Conyza canadensis; also commonly known as horseweed) sprayed with glyphosate (Roundup®) are incubated in a cocktail mixture with 0 mM glyphosate and a volume of crude extract of GOX expressing canola leaves. Alternatively, the GOX that is used may be isolated and/or extracted from microorganisms. The disclosed procedures for signal detection and analysis as described may be used to image glyphosate in the marestail plant tissue.

Detection and quantitation of glyphosate in plant tissue may identify local distribution and translocation of the herbicide through plant tissue, including enzymes that breakdown glyphosate. In contrast to other methods, which employ techniques such as HPLC, the present methods use very small sample volumes and no chemical extraction procedures are required for glyphosate imaging and quantitation.

The present methods and compositions can be applied to detect and/or quantitate glyphosate in other samples besides plant tissue. For example, glyphosate may be visualized and/or quantified by light emission in various biological samples including microorganisms, such as bacteria, algae, protozoa, and fungi, among others. As described herein with respect to plant tissue, the microorganism(s) is contacted with an enzyme cocktail, where the enzyme cocktail includes oxidized nicotinamide adenine dinucleotide phosphate (NADP+), glyphosate oxidoreductase (GOX), flavin mononucleotide (FMN), flavin oxidoreductase, a long-chain fatty aldehyde, and luciferase. Light emission from the microorganism(s) is measured, with light emission proportional to glyphosate in the microorganism(s). In some cases, the microorganism may express glyphosate oxidoreductase (GOX) so that the enzyme cocktail may not need to include glyphosate oxidoreductase (GOX), as per plant tissue expressing glyphosate oxidoreductase (GOX). Also, as described herein with respect to plant tissue, cellular enzymes in the microorganism(s) may be inactivated by heating prior to the contacting and reduced nucleotides in the microorganism(s) may be selectively removed by acid treatment prior to the contacting.

Glyphosate may further be visualized and/or quantified by light emission in other samples, including soil and water. For example, the light emission from the present methods and compositions can be used to measure the amount of glyphosate in the sample. Comparison with a glyphosate standard curve, for example similar to that shown in FIG. 7, would allow determination of the amount of glyphosate in a water or soil sample. As described, an increase in the amount of light detected (bioluminescence) is observed with an increase in glyphosate concentration.

All literature and similar materials cited in this disclosure, including but not limited to, patents, patent applications, articles, books, treatises, and internet web pages, regardless of the format of such literature and similar materials, are expressly incorporated by reference in their entirety for any purpose. In the event that one or more of the incorporated literature and similar materials differs from or contradicts this disclosure, including but not limited to defined terms, term usage, described techniques, or the like, this disclosure controls.

The description of the technology is merely exemplary in nature and, thus, variations that do not depart from the gist of the present invention are intended to be within the scope of the invention. Such variations are not to be regarded as a departure from the spirit and scope of the invention.

What is claimed is:

1. A method for detecting glyphosate in plant tissue expressing glyphosate oxidoreductase (GOX) comprising:
   contacting the plant tissue with an enzyme cocktail, the enzyme cocktail comprising oxidized nicotinamide adenine dinucleotide phosphate ($NADP^+$), flavin mononucleotide (FMN), flavin oxidoreductase, a long-chain fatty aldehyde, and luciferase; and
   detecting light emission from the plant tissue.

2. The method of claim 1, wherein cellular enzymes in the plant tissue are inactivated by heating prior to the contacting.

3. The method of claim 1, wherein reduced nucleotides in the plant tissue are selectively removed by acid treatment prior to the contacting, the acid treatment comprising treating the plant tissue with acid and neutralizing the acid.

4. The method of claim 3, wherein the acid treatment comprises:
   treating the plant tissue with HCl and ascorbic acid;
   adding additional HCl to the plant tissue; and
   neutralizing the plant tissue with NaOH and $K_2HPO_4$.

5. The method of claim 1, wherein detecting comprises measuring light emission during a discrete time interval.

6. The method of claim 1, wherein detecting light emission from the plant tissue comprises recording an image of the light emitted from the plant tissue.

7. The method of claim 1, further comprising comparing the light emitted from the plant tissue to the light emitted from at least one volume comprising a known amount of glyphosate, enzyme cocktail, and glyphosate oxidoreductase (GOX) to quantify the amount of glyphosate in the plant tissue.

8. A method for detecting glyphosate in a sample comprising:
   contacting the sample with an enzyme cocktail, the enzyme cocktail comprising oxidized nicotinamide adenine dinucleotide phosphate ($NADP^+$), glyphosate oxidoreductase (GOX), flavin mononucleotide (FMN), flavin oxidoreductase, a long-chain fatty aldehyde, and luciferase; and
   detecting light emission from the sample.

9. The method of claim 8, wherein the sample comprises a microorganism.

10. The method of claim 8, wherein the sample comprises water or soil.

11. The method of claim 8, wherein the sample comprises plant tissue.

12. The method of claim 8, wherein cellular enzymes in the sample are inactivated by heating prior to the contacting.

13. The method of claim 8, wherein reduced nucleotides in the sample are selectively removed by acid treatment prior to the contacting, the acid treatment comprising treating the sample with acid and neutralizing the acid.

14. The method of claim 13, wherein the acid treatment comprises:
   treating the sample with HCl and ascorbic acid;
   adding additional HCl to the sample; and
   neutralizing the sample with NaOH and $K_2HPO_4$.

15. The method of claim 8, wherein detecting comprises measuring light emission during a discrete time interval.

16. The method of claim 8, wherein detecting light emission from the sample comprises recording an image of the light emitted from the sample.

17. The method of claim 8, further comprising comparing the light emitted from the sample to the light emitted from at least one volume comprising a known amount of glyphosate and the enzyme cocktail.

18. A kit for quantifying glyphosate in plant tissue comprising:
   oxidized nicotinamide adenine dinucleotide phosphate ($NADP^+$);
   glyphosate oxidoreductase (GOX);
   flavin mononucleotide (FMN);
   flavin oxidoreductase;
   a long-chain fatty aldehyde; and
   luciferase.

19. The kit of claim 18, further comprising glyphosate.

20. The kit of claim 18, wherein the glyphosate oxidoreductase (GOX) is packaged separately from the oxidized nicotinamide adenine dinucleotide phosphate ($NADP^+$), flavin mononucleotide (FMN), flavin oxidoreductase, a long-chain fatty aldehyde, and luciferase.

* * * * *